(12) United States Patent
Zhao

(10) Patent No.: US 11,766,165 B2
(45) Date of Patent: Sep. 26, 2023

(54) OPTICAL SYSTEM AND STEREO-VIDEO ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 432 days.

(21) Appl. No.: 17/140,217

(22) Filed: Jan. 4, 2021

(65) Prior Publication Data

US 2021/0121050 A1    Apr. 29, 2021

Related U.S. Application Data

(63) Continuation of application No. PCT/EP2019/066137, filed on Jun. 19, 2019.

(30) Foreign Application Priority Data

Jul. 4, 2018 (DE) .......................... 102018116139.5

(51) Int. Cl.
   *A61B 1/00* (2006.01)
(52) U.S. Cl.
   CPC ...... *A61B 1/00193* (2013.01); *A61B 1/00183* (2013.01); *A61B 1/00195* (2013.01)
(58) Field of Classification Search
   CPC ...... A61B 1/00183; A61B 1/193; A61B 1/195
   See application file for complete search history.

(56) References Cited

U.S. PATENT DOCUMENTS

| 6,239,922 | B1 | 5/2001 | Nakamura |
| 6,361,491 | B1 | 3/2002 | Hasegawa et al. |
| 10,088,665 | B2 | 10/2018 | Zhao et al. |
| 2009/0160935 | A1 | 6/2009 | Rovegno et al. |

(Continued)

FOREIGN PATENT DOCUMENTS

| DE | 102013215422 A1 | 2/2015 |
| DE | 102017123896.4 A1 | 4/2019 |
| EP | 2806301 A1 | 11/2014 |

(Continued)

OTHER PUBLICATIONS

International Search Report dated Sep. 24, 2019 issued in PCT/EP2019/066137.

*Primary Examiner* — Aaron B Fairchild
(74) *Attorney, Agent, or Firm* — Scully, Scott, Murphy & Presser, P.C.

(57) ABSTRACT

An optical system for a stereo-video endoscope, the optical system including: first and second lens system channels having first and second optical elements on first and second optical axes, respectively, the first and second optical axes being parallel to each other; wherein the first and second optical elements are each arranged symmetrically relative to each other about a plane of symmetry between the first and second lens system channels and the first and second optical elements comprise first and second D-cut lenses, respectively, each of the first and second D-cut lenses having a boundary surface which is set back relative to the plane of symmetry; and the boundary surface of each of the first and second D-cut lenses are inclined with respect of the plane of symmetry.

13 Claims, 2 Drawing Sheets

(56) References Cited

U.S. PATENT DOCUMENTS

2014/0177043 A1    6/2014  Togino et al.
2018/0295265 A1*  10/2018  Suga .................. G02B 7/06

FOREIGN PATENT DOCUMENTS

| JP | H08-56891 A | 3/1996 |
| JP | H09-127435 A | 5/1997 |
| JP | 2013-217947 A | 10/2013 |

* cited by examiner

Fig. 1a) (Prior Art)
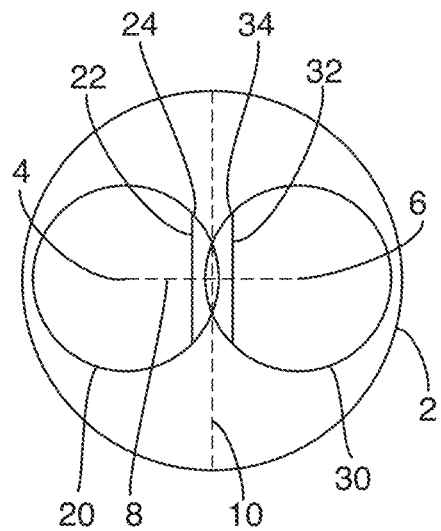
Fig. 1b) (Prior Art)
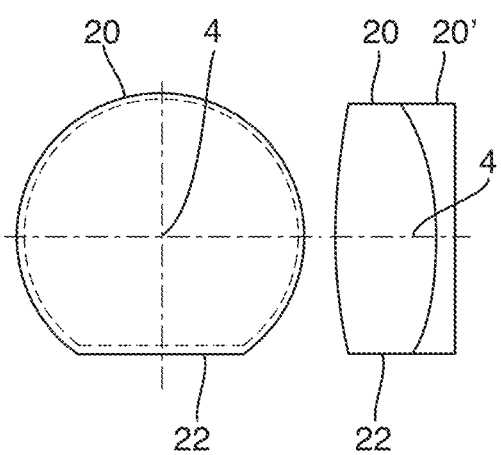
Fig. 2a) (Prior Art)
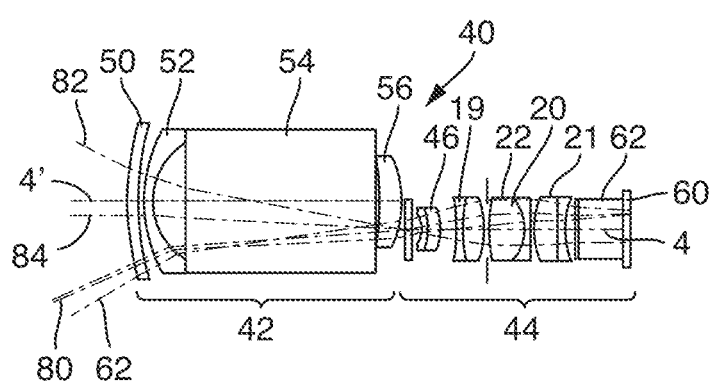
Fig. 2b) (Prior Art)
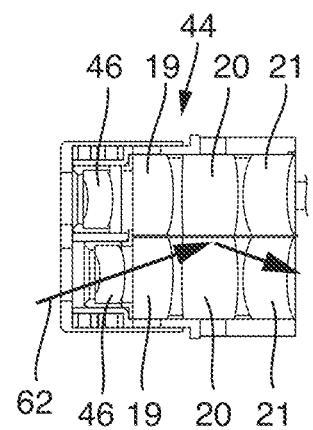
Fig. 3 (Prior Art)
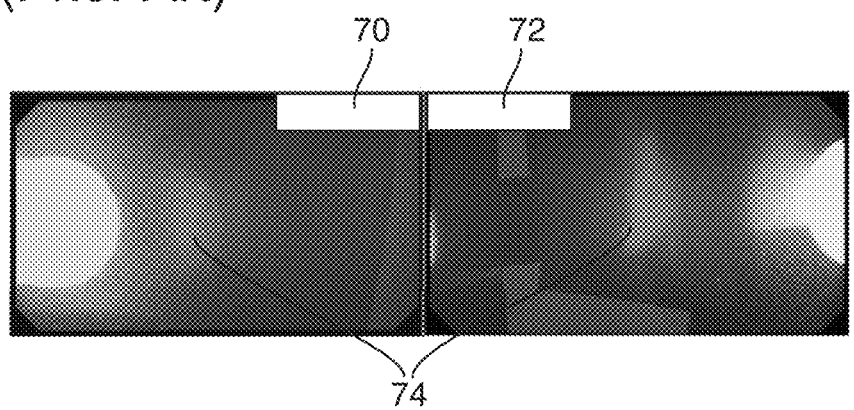

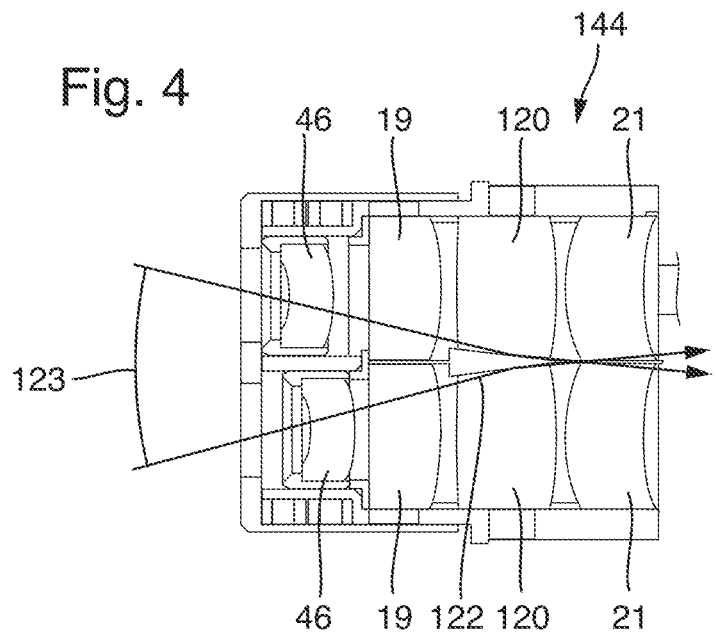
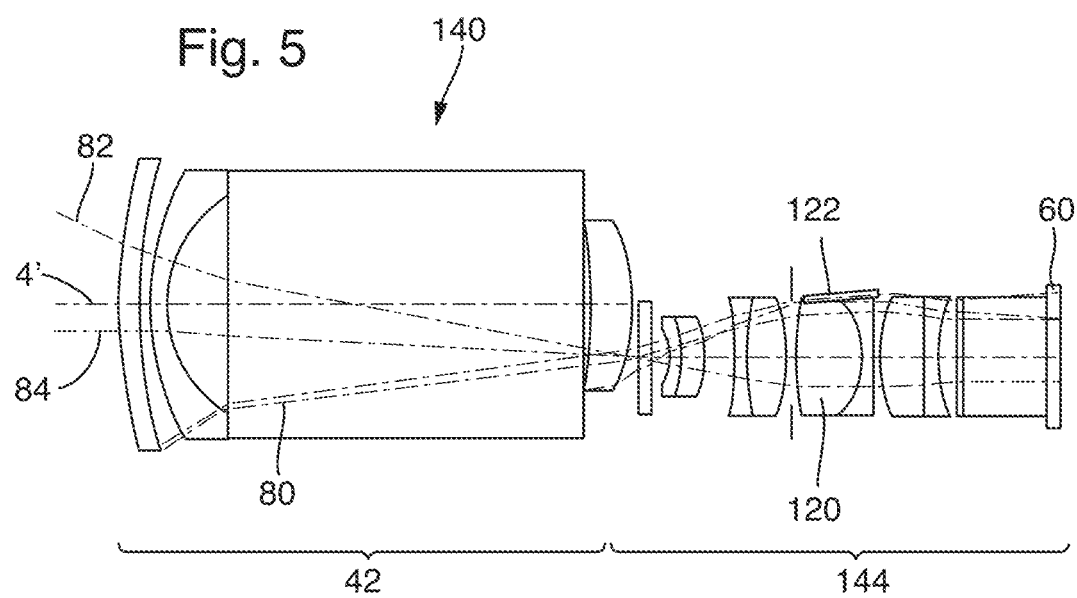

OPTICAL SYSTEM AND STEREO-VIDEO ENDOSCOPE

CROSS-REFERENCE TO RELATED APPLICATION

The present application is a continuation of PCT/EP2019/066137 filed on Jun. 19, 2019, which is based upon and claims the benefit to DE 10 2018 116 139.5 filed on Jul. 4, 2018, the entire contents of each of which are incorporated herein by reference.

BACKGROUND

Field

The present disclosure relates to an optical system for a stereo-video endoscope, which has, at least in sections, two separate lens system channels for a left and a right channel having one or more pairs of optical elements on optical axes which are parallel to each other. The present disclosure further relates to a corresponding stereo-video endoscope.

Prior Art

Stereo-video endoscopes are deployed in medicine to provide a treating physician with a spatial representation of the interior of a patient's body. To this end, light bundles entering an optical system of the endoscope are guided in two parallel running and configured lens system channels, which depict the light bundles on two separate image sensors. In this way, images of the observed region are captured at slightly varying viewing angles. If these images are observed such that each eye in each case perceives the image or the images of one lens system channel, for example with the aid of shutter glasses, a spatial impression of the observed region is created. This is referred to as stereoscopy. A corresponding stereo-video endoscope is disclosed, for example, in DE 10 2013 215 422 A1.

The challenge with stereoscopic endoscopes is to construct the stereo base, which is important for the spatial impression, so that it is sufficiently large, while the outer diameter of the endoscope shaft is to be kept as small as possible. One difficulty arises from the fact that the optical elements arranged in the lens system channels are to have as large a cross-sectional area as possible so that a high light throughput and a high image quality are attained. Admittedly, if the optical elements are too large, they no longer fit next to each other in the casing tube of the endoscope. Furthermore, additional care must be taken to ensure that the correct distance of the optical axes is observed, even in the case of large optical elements.

One solution to this optimization problem is described in the applicant's German patent application which has the official file number DE 10 2017 123 896.4. A compromise between the largest possible active surface of the optical elements of the lens system channels and as small as possible a diameter of the casing tube is brought about in that the optical elements, in this case circular lenses, are each cut or ground off on one side, so that a boundary surface is created, which substantially lends the lens the form of a letter "D". Lenses processed in such a way are also designated "D-cut" lenses. Said boundary surfaces make it possible for the D-cut lenses to be arranged closer to each other than would be the case with unprocessed lenses. Conversely, this means that when the distance of the optical axes from each other is the same, the cross-sectional area of the D-cut lenses can be significantly larger than that of unprocessed lenses having a round cross-section. The altered geometry results in an increased utilization of the cross-sectional area in the casing tube of the endoscope.

FIGS. 1a) and 1b) show schematic sectional representations of known D-cut lenses, as described in the applicant's German patent application which has the official file number DE 10 2017 123 896.4.

In FIG. 1a), a cross-section through the casing tube 2 of a stereo-video endoscope is shown, in which a left and a right image channel are each provided with their own lens system channels which each have pairs of optical elements, such as lenses, in a completely or largely symmetrical arrangement. In the case shown, these are D-cut lenses 20, 30 which are provided with set-back boundary surfaces 22, 32 so that they can be located closer to each other in the casing tube 2 than would be possible due to the circumferential circles 24, 34 without the corresponding boundary surfaces 22, 32. This makes it possible, with a simultaneously relatively large light-harvesting surface, to adjust a desired distance of the optical axes 4, 6 of the left and of the right image channel or respectively of the left and right lens channel systems. The boundary surfaces 22, 32 are realized as flat cuts which are aligned parallel to a plane of symmetry 10 which is arranged in the middle between and in each case perpendicular to the optical axes 4, 6. The plane of symmetry 10 is also perpendicular to a connecting line 8 between the optical axes 4, 6.

In FIG. 1b), the D-cut lens 20 is shown, on the one hand, in a cross-section perpendicular to the optical axis 4 (left-hand representation) and, on the other hand, in a cross-section along the connecting line 8 from FIG. 1a) (right-hand representation). This is, in this case, a lens group made of a biconvex lens 20 and a planoconcave lens 20' which are both configured as a D-cut lens. The boundary surfaces 22 are, in both cases, arranged flat and parallel to the optical axis 4, which causes the optical axis 4 to not be arranged centrally in the D-cut lens 20, 20'.

FIG. 2a) represents a beam path through an optical system 40 of a stereo-video endoscope which has a section having a common lens system 42 as well as a section 44 having a separate lens channel system, only one lens channel system of which is actually represented for the sake of simplicity. The second channel system would be arranged symmetrically to the lower lens channel system above the plane of symmetry which is formed as a continuation of the optical axis 4' of the optical system 40 in the region of the common lens systems 42.

The common lens system 42 is composed, in the exemplary embodiment, of an inlet window 50, an inlet lens 52 configured as a negative meniscus, a prism 54 which deflects the beams in the depth plane of the representation so that the optical beams do not appear to be bent in the view shown, as well as an outlet lens 56. Joined to the outlet lens 56 is an inlet window (without reference numeral) of the lens channel system shown, as well as an axially displaceable lens or respectively lens group 46 which, in the case of a sideways looking endoscope, offsets differences in the beam path of the right and of the left channel, as well as three lens groups 19, 20, 21 which are configured as D-cut lenses. The image sensor 60 follows.

Likewise represented are multiple possible beam paths, wherein the boundary beam path 80 for the outermost edge of the direct field of view is highlighted with a thicker dot-dashed line. The central axis of the beam path 84 for the lens channel system 44 is likewise represented with a thicker dot-dashed line, while the inner bounding beam path 82 is represented with a solid line. A region outside of the actual field of view is additionally represented with a beam path 62 which can lead to ghost images, since, in the course of the optical system, it strikes the boundary surface 22 of the D-cut lens or respectively D-cut lens group 20 and, from there, it is reflected again into the beam path so that it strikes the image sensor 60 as a ghost image. This is represented in the larger depiction in FIG. 2b) for the section having the parallel lens channel systems.

FIG. 3 represents a ghost image effect 74 in a left channel 70 and a right channel 72 of a stereo-video endoscope having an optical system according to FIG. 2. The ghost images appearing approximately in the middle are created by a reflection off the boundary surfaces 22 of the D-cut lenses 20.

SUMMARY

An object is to improve the optical characteristics of stereo-video endoscopes having D-cut lenses.

Such object can be achieved by an optical system for a stereo-video endoscope, which has, at least in sections, two separate lens system channels for a left and a right channel having one or more pairs of optical elements on optical axes which are parallel to each other, wherein the optical elements of one or more of the pairs of optical elements are each arranged symmetrically relative to each other about a plane of symmetry between the lens system channels and at least one pair of optical elements arranged symmetrically relative to each other is configured as a pair of D-cut lenses, each of which have a boundary surface which is set back relative to the plane of symmetry and can be flat, wherein the boundary surfaces of the D-cut lenses of the pair are each inclined in respect of the plane of symmetry.

In the case of the stereo-video endoscopes described in the applicant's patent application DE 10 2017 123 896.4, it has emerged that when stronger sources of light are present outside of the direct field of view of the stereo-video endoscope, disturbing ghost images can be created, which, as a result of reflection off the boundary surfaces, travel into the sensor region of the image sensors. In some configurations, it was then not possible to suppress this by suitable diaphragms in the beam path. In embodiments, the inclination of the boundary surfaces of the D-cut lenses of the D-cut lens pair can be configured to divert light beams from regions outside of a field of view of the optical system, which are reflected off the boundary surfaces, such that they do not travel into optical image sensors which are assigned to the lens system channels. Either separate image sensors can be assigned to the left and right channels or a large image sensor is used, which is illuminated in two different regions by the left or respectively right lens system channel.

The exact alignment of the boundary surfaces in the optical system depends on the total configuration of the optical system and requires the observation of beams from inside and outside of the direct field of view, which can strike the boundary surfaces and which cannot be blocked by suitably located diaphragms, as well as the path thereof in the further course from the boundary surfaces to the image sensors. The inclination of the boundary surfaces can then be adjusted such that those beams which would lead to disturbing ghost images are diverted and no longer strike the image sensors.

Within the context of the present disclosure, the term "D-cut lenses" is also understood to be a lens group having corresponding boundary surfaces which are in each case combined into one lens unit, for example using optical cement.

In embodiments, normals to the boundary surfaces of the D-cut lenses of the D-cut lens pair can lie in the plane which is spanned by the optical axes of the two lens system channels. The normals are straight lines which are perpendicular to the boundary surfaces, such as those which run through the respective center of the boundary surfaces. In a reference system, in which the two lens channel systems are defined as right and left, the boundary surfaces do not need to be inclined upwards or downwards, that is to say about a horizontal axis in the direction of the optical axis, but can be inclined only about a vertical axis.

In embodiments, the normals to the boundary surfaces of the D-cut lenses of the D-cut lens pair can intersect on a line in the middle between the two optical axes. This means that the inclination of the two boundary surfaces of the pair of D-cut lenses can be mirror-symmetric with respect to each other.

In embodiments, the normals to the boundary surfaces of the D-cut lenses of the D-cut lens pair can be each at an angle of 2° to 30°, such as 5° to 15°, to a connecting line between the centers of the two D-cut lenses. Depending on the total configuration of the optical system, these angular ranges can provide a balance of suppressing ghost images and a small width of the necessary gap between the pair of D-cut lenses.

The boundary surfaces of the D-cut lenses of the D-cut lens pair can be inclined such that the distance between the boundary surfaces decreases in a direction of incident light of the optical system from distal to proximal. As a result, marginal beams can strike the boundary surfaces at a flatter angle and can be reflected at a flatter angle such that they no longer strike the image sensors. This simultaneously avoids the boundary surfaces projecting into the beam path due to their inclination.

In embodiments, where D-cut lens groups are made of multiple different D-cut lenses connected to each other, the boundary surfaces can align with each other or have different inclinations. In a further embodiment, the boundary surfaces of a D-cut lens group can have a stepped arrangement. Such a stepping of the inclinations can be useful in order to take account of different optical characteristics of the individual lenses of the lens group as well as of the total course of the beam paths of the optical system. If the inclination of the boundary surfaces of the rear, that is to say the proximal, lens is less than that of the front, that is to say distal, lens of the lens group, a sufficient distance can remain between the D-cut lenses of the pair arranged symmetrically on both sides of the plane of symmetry and, simultaneously, the light-harvesting surface of the lens can remain large.

The boundary surfaces of the D-cut lenses of the D-cut lens pair can be treated in a low-reflection manner, such as sanded smooth or roughened, and/or coated in a light-absorbing manner. These measures can further reduce the quantity of the available light for disturbing ghost images.

Such object can also be achieved by a stereo-video endoscope having an optical system as described above. Said stereo-video endoscope can therefore implement the same features, characteristics and advantages as the optical system described above.

BRIEF DESCRIPTION OF THE DRAWINGS

Further features will become evident from the description of embodiments, together with the claims and the appended drawings. Embodiments can fulfill individual features or a combination of multiple features.

The embodiments are described below without limiting the general concept of the invention by means of exemplary embodiments with reference to the drawings, wherein reference is expressly made to the drawings regarding all of the details which are not explained in greater detail in the text, wherein:

FIGS. 1a) and 1b) illustrate schematic sectional representations of known D-cut lenses, FIGS. 2a) and 2b) illustrate a schematic representation of the beam path of a known stereo-video endoscope having D-cut lenses, FIG. 3 illustrates a ghost image effect, FIG. 4 illustrates a part of an optical system having D-cut lenses, and FIG. 5 illustrates a beam path of a part of an optical system having D-cut lenses.

In the drawings, the same or similar elements and/or parts are, in each case, provided with the same reference numerals such that they are not introduced again in each case.

DETAILED DESCRIPTION

FIG. 4 shows a section 144 of an optical system having two parallel lens system channels having D-cut lenses 120. The representation corresponds to that of FIG. 2b), with the difference that the D-cut lenses or respectively D-cut lens groups 120 are provided with inclined boundary surfaces 122. The inclination is, in this case, mirror-symmetric and opposed in the two lens channel systems for the right and left channel, so that an aperture angle 123 is produced in the direction of the distal end (represented pointing left), which has double the amount of the angle of inclination of the boundary surfaces 122 of each individual D-cut lens 120.

It is likewise visible that the two lenses of the lens group which form the D-cut lens 120 have rather different angles of inclination and that a step is present at their transition. This steplike configuration contributes, on the one hand, to the fact that the lens group can be easily positioned at corresponding stops of the holding device, and allows varying optical characteristics of the two lenses of the lens group 120 to be considered. Thus, it is possible to adjust the angle of inclination of the proximal lens of the lens group 120 so that it is less than that of the distal lens of the lens group 120, saving space with respect to the plane of symmetry.

Finally, those skilled in the art will appreciate that, in this view, the axially displaceable lenses 46 or respectively lens groups of the two lens system channels at the entrance of the assembly are arranged at various axial positions. This therefore offsets a difference in the beam path in the case of a sideways looking endoscope, the viewing direction of which is at an angle to the plane of symmetry (into the plane of the figure).

Following FIG. 4, FIG. 5 shows a beam path of a part of an optical system 140 having a section 144 having D-cut lenses 120, substantially in the optical configuration represented in FIG. 4. In addition to the optical axis 4' of the common system 42, the boundary beam paths 80, 82 and the central beam path 84 of the direct field of view are also represented. There is no risk of reflection off the boundary surfaces 122 for beams from outside of the direct field of view, since said boundary surfaces are correspondingly set back with their inclination, so that no reflection back to the beam path and onto the image sensor 60 occurs.

The boundary surfaces 122 of the D-cut lenses 120 can be processed in a low-reflection manner, for example by a light-absorbing coating on a boundary surface which has been processed by roughening or smooth sanding, in order to suppress the occurrence of disturbing ghost images to an even greater extent.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Casing tube
4, 4' Optical axis
6 Optical axis
8 Connecting line
10 Plane of symmetry
19 Lenses
20, 120 D-cut lens
20' D-cut lens
21 D-cut lens
22, 122 Boundary surface
24 Circumferential circle
30 D-cut lens
32 Boundary surface
34 Circumferential circle
40, 140 Optical system
42 Common lens system
44, 144 Section having separate lens channel systems
46 Axially displaceable lens
50 Inlet window
52 Inlet lens
54 Prism
56 Outlet lens
60 Image sensor
62 Beam path for ghost image
70 Left channel
72 Right channel
74 Ghost image
80 Outer boundary beam path
82 Inner boundary beam path
84 Central beam path
123 Aperture angle

What is claimed is:

1. An optical system for a stereo-video endoscope, the optical system comprising:
   first and second lens systems having first and second optical elements on first and second optical axes, respectively, the first and second optical axes being parallel to each other;
   wherein the first and second optical elements are each arranged symmetrically relative to each other about a plane of symmetry between the first and second lens systems and the first and second optical elements comprise first and second D-cut lenses, respectively, each of the first and second D-cut lenses having a boundary surface which is set back relative to the plane of symmetry; and
   the boundary surface of each of the first and second D-cut lenses are inclined with respect of the plane of symmetry.

2. The optical system according to claim 1, wherein the boundary surface for each of the first and second D-cut lenses is flat.

3. The optical system according to claim 1, wherein the inclination of the boundary surfaces of each of the first and second D-cut lenses is configured to divert light beams from regions outside of a field of view of the optical system, which are reflected off the boundary surface of each of the first and second D-cut lenses, such that the light beams do not travel into first and second optical image sensors provided to the first and second lens systems, respectively.

4. The optical system according to claim 1, wherein a normal to the boundary surface of each of the first and second D-cut lenses lie in the plane which is spanned by the first and second optical axes of the first and second lens systems, respectively.

5. The optical system according to claim 3, wherein the normal to the boundary surface of each of the first and second D-cut lenses intersect on a line in a middle between the first and second optical axes.

6. The optical system according to claim 3, wherein the normal to the boundary surface of each of the first and second D-cut lenses is at an angle of 2° to 30° to a connecting line between centers of the first and second D-cut lenses.

7. The optical system according to claim 6, wherein the normal to the boundary surface of each of the first and second D-cut lenses is at the angle of 5° to 15° to the connecting line between the centers of the first and second D-cut lenses.

8. The optical system according to claim 1, wherein the boundary surface of each the first and second D-cut lenses is inclined such that a distance between the boundary surface decreases proximally in a direction of incident light of the optical system.

9. The optical system according to claim 1, further comprising D-cut lens groups comprising multiple different D-cut lenses connected to each other, wherein boundary surfaces of each of the multiple different D-cut lenses align with each other or have different inclinations.

10. The optical system according to claim 1, further comprising D-cut lens groups comprising multiple different D-cut lenses connected to each other, wherein boundary surfaces of each of the multiple different D-cut lenses form a stepped arrangement.

11. The optical system according to claim 1, wherein the boundary surface of each of the first and second D-cut lenses further comprise a low-reflection surface.

12. The optical system according to claim 11, wherein the low-reflection surface comprises one or more of a sanded smooth surface, a roughened surface and a coated surface.

13. A stereo-video endoscope having the optical system according to claim 1.

* * * * *